US007998158B2

(12) United States Patent
Fletcher et al.

(10) Patent No.: US 7,998,158 B2
(45) Date of Patent: Aug. 16, 2011

(54) SURGICAL SAW BLADE HAVING AT LEAST ONE PAIR OF OPPOSED TEETH SHAPED AS RIGHT TRIANGLES

(75) Inventors: Henry Hasbrouck Fletcher, Cameron Park, CA (US); Michael Gerard Fisher, Folsom, CA (US)

(73) Assignee: Synvasive Technology, Inc., Reno, NV (US)

( * ) Notice: Subject to any disclaimer, the term of this patent is extended or adjusted under 35 U.S.C. 154(b) by 303 days.

(21) Appl. No.: 12/330,063

(22) Filed: Dec. 8, 2008

(65) Prior Publication Data

US 2009/0093815 A1    Apr. 9, 2009

Related U.S. Application Data

(60) Division of application No. 10/826,209, filed on Apr. 16, 2004, now Pat. No. 7,527,628, which is a continuation-in-part of application No. 10/071,382, filed on Feb. 6, 2002, now Pat. No. 6,723,101, which is a continuation of application No. 09/499,803, filed on Feb. 8, 2000, now Pat. No. 6,503,253, which is a continuation of application No. 08/153,871, filed on Nov. 16, 1993, now Pat. No. 6,022,353, which is a continuation of application No. 07/707,903, filed on May 30, 1991, now abandoned.

(51) Int. Cl.
*A61F 17/14*    (2006.01)
(52) U.S. Cl. ............................................ 606/176; 178/79
(58) Field of Classification Search .................... 606/79, 606/82, 84, 167, 176–178; 83/844, 852
See application file for complete search history.

(56) References Cited

U.S. PATENT DOCUMENTS

| 2,455,655 A | 12/1948 | Carroll ........................... 606/178 |
| 2,795,247 A | 6/1957 | Topolinski ....................... 83/848 |
| 3,901,117 A | 8/1975 | Hoffman .......................... 83/698 |
| 3,905,105 A | 9/1975 | Tuke ............................. 606/176 |

(Continued)

FOREIGN PATENT DOCUMENTS

EP     0382483     8/1990

(Continued)

OTHER PUBLICATIONS

Stryker Drawing No. 0277-534-053; Jun. 2009; One (1) page; Sagittal Blade (5.0mm Cut Edge).

(Continued)

*Primary Examiner* — Michael A. Brown
(74) *Attorney, Agent, or Firm* — Knobbe, Martens, Olson & Bear LLP

(57) ABSTRACT

A cutting saw blade for use with an oscillatory power tool used in surgical bone cutting procedures including a blade having a distal end provided with teeth whose tips are located on a tangent line perpendicular to the long axis of the blade. The teeth are configured substantially as right triangles with their hypotenuses facing either towards the center of the blade or away from the center of the blade. A central tooth can be optionally provided. The surgical saw blade may have a distal end having at least one pair of teeth configured to be adjacent to each other and each of the pair of teeth is configured as a right triangle each having a hypotenuse which is oriented at least one of towards and away from the centrally positioned long axis.

13 Claims, 9 Drawing Sheets

U.S. PATENT DOCUMENTS

| | | | |
|---|---|---|---|
| 3,905,374 A | 9/1975 | Winter | 606/178 |
| 3,943,934 A | 3/1976 | Bent | 606/178 |
| 4,012,978 A | 3/1977 | De Lanauze | 83/698 |
| 4,069,824 A | 1/1978 | Weinstock | 606/82 |
| 4,386,609 A | 6/1983 | Mongeon | 606/178 |
| 4,513,742 A | 4/1985 | Arnegger | 606/178 |
| 4,584,999 A | 4/1986 | Arnegger | 606/178 |
| 4,594,781 A | 6/1986 | Hoffman | 83/698 |
| 4,922,612 A | 5/1990 | Greenwood | 606/178 |
| 5,122,142 A | 6/1992 | Pascaloff | 606/178 |
| 5,133,728 A * | 7/1992 | Petersen | 606/176 |
| 5,135,533 A * | 8/1992 | Petersen et al. | 606/176 |
| D337,160 S | 7/1993 | Evans | D24/146 |
| 5,263,972 A | 11/1993 | Evans | 606/176 |
| 5,306,285 A | 4/1994 | Miller et al. | 606/177 |
| 5,382,249 A | 1/1995 | Fletcher | 606/79 |
| 5,439,472 A | 8/1995 | Evans et al. | 606/176 |
| 6,022,353 A | 2/2000 | Fletcher et al. | 606/79 |
| 6,503,253 B1 | 1/2003 | Fletcher et al. | 606/79 |
| 6,723,101 B2 | 4/2004 | Fletcher et al. | 606/176 |
| 7,527,628 B2 | 5/2009 | Fletcher et al. | 606/179 |
| 2003/0032971 A1 | 2/2003 | Hausmann et al. | 606/176 |
| 2003/0199880 A1 | 10/2003 | Meckel | 606/82 |

FOREIGN PATENT DOCUMENTS

| | | |
|---|---|---|
| EP | 0884142 | 12/1998 |

OTHER PUBLICATIONS

Statement of Gregory W. May with Exhibit A, May 20, 1996; Co-Owner of Trimed, Inc.; Re: Trial Surgical Sagittal Saw Blade disclosed and offered for sale by Trimed, Inc. in 1988.

Micro-Aire.TM. Catalog: "Accessories-Orthopedic Power Instrument System".

Stryker.RTM. Surgical Catalog: "Cutting Accessories Guide".

Hall Surgical Catalog: "Hall Quality Saw Blades for Stryker and 3M".

U.S. Appl. No. 07/707,903, filed May 30, 1991, Fletcher.

* cited by examiner

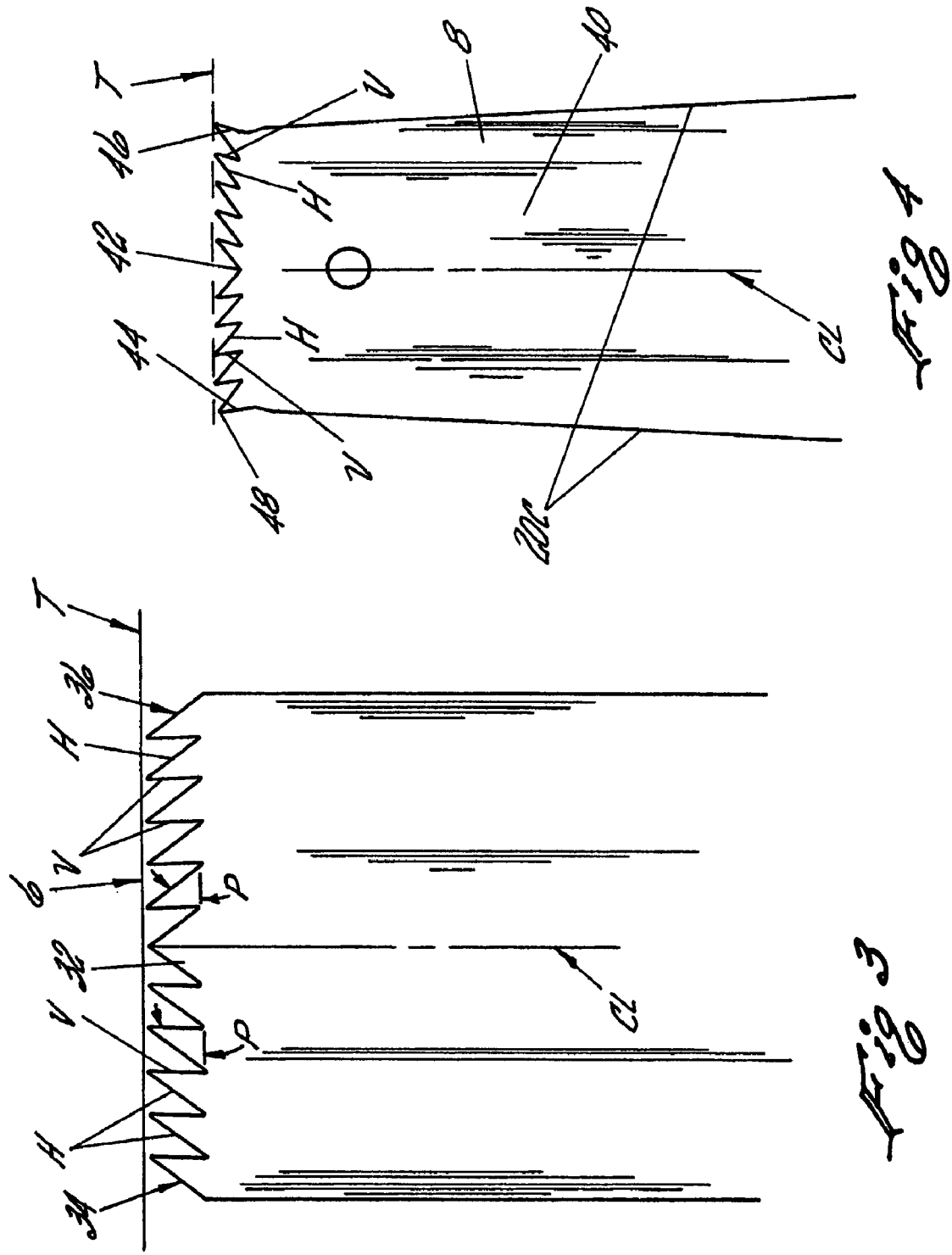

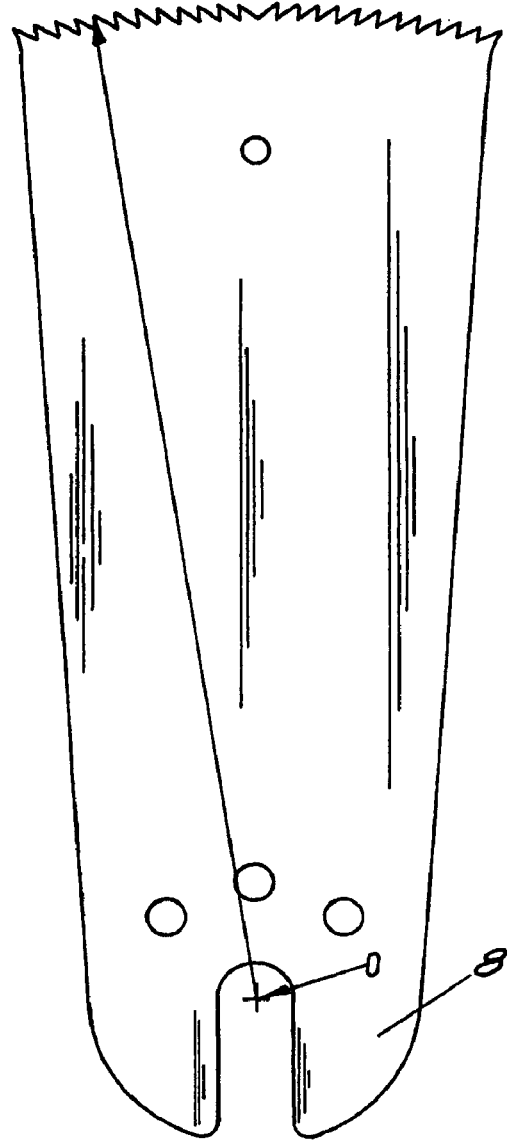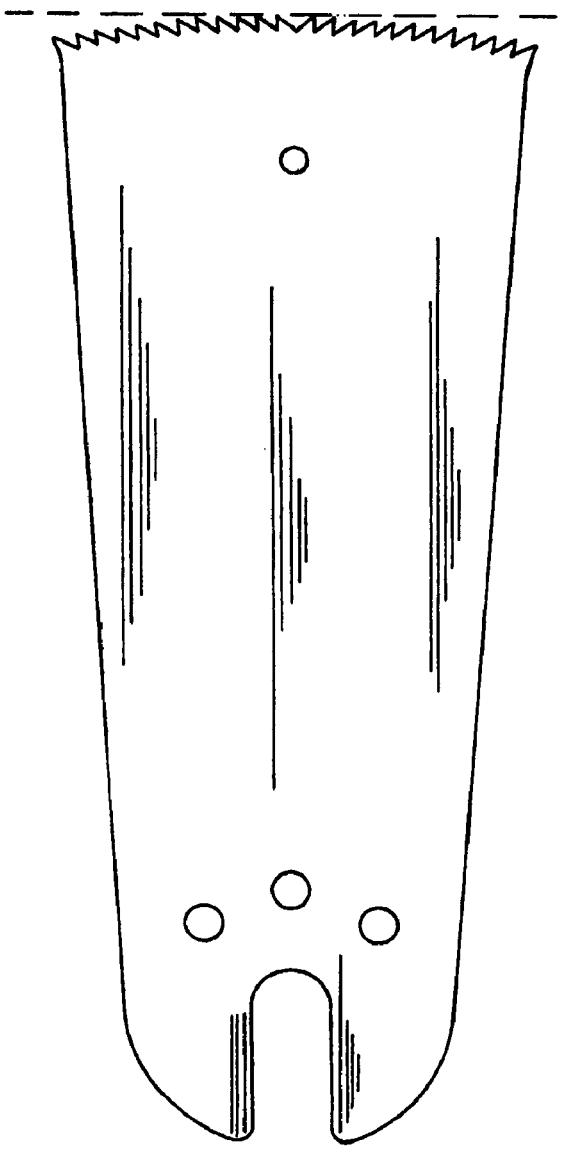
PRIOR ART
Fig 6A
PRIOR ART
Fig 6B

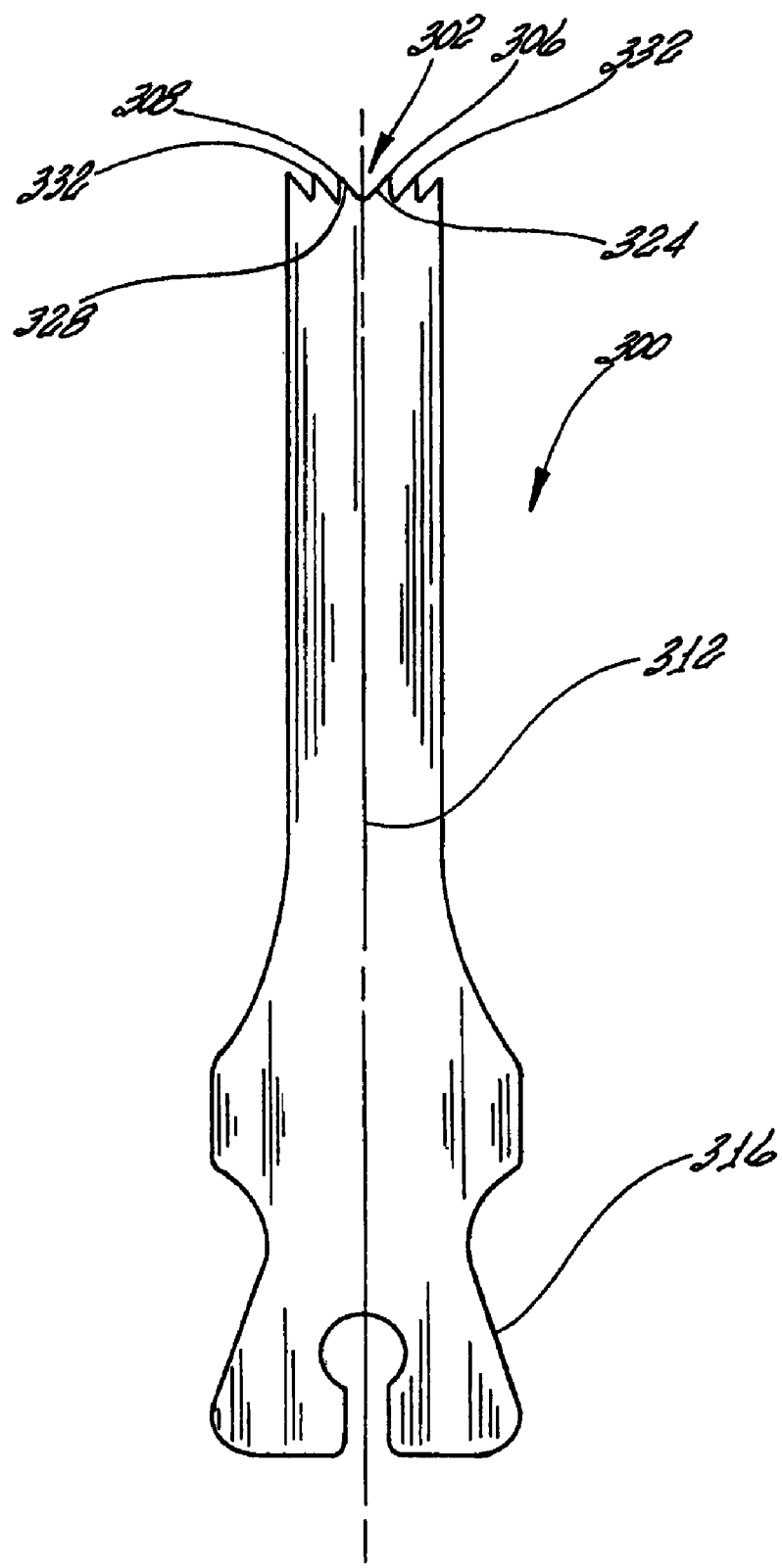

SURGICAL SAW BLADE HAVING AT LEAST ONE PAIR OF OPPOSED TEETH SHAPED AS RIGHT TRIANGLES

CROSS-REFERENCES TO RELATED APPLICATIONS

This application is a Divisional Application of U.S. patent application Ser. No. 10/826,209 filed on Apr. 16, 2004, now U.S. Pat. No. 7,527,628 which is a Continuation-in-Part of U.S. patent application Ser. No. 10/071,382 filed on Feb. 6, 2002, issued as U.S. Pat. No. 6,723,101 on Apr. 20, 2004, which is a Continuation of U.S. patent application Ser. No. 09/499,803 filed on Feb. 8, 2000, issued as U.S. Pat. No. 6,503,253 on Jan. 7, 2003, which is a Continuation of U.S. patent application Ser. No. 08/153,871 filed on Nov. 16, 1993, issued as U.S. Pat. No. 6,022,353 on Feb. 8, 2000, which is a Continuation of U.S. patent application Ser. No. 07/707,903 filed May 30, 1991, abandoned.

STATEMENT REGARDING FEDERALLY SPONSORED RESEARCH OR DEVELOPMENT

Not Applicable

REFERENCE TO A "MICROFICHE APPENDIX" (SEE 37 CFR 1.96)

Not Applicable

BACKGROUND OF THE INVENTION

1. Field of the Invention

The following invention relates generally to instrumentalities for cutting bone during surgery. More particularly, the instant invention is directed to a saw blade adapted to be operatively coupled to an oscillatory (or sagittal) surgical power tool which reciprocates the cutting blade back and forth about a small arc. In the preferred embodiment, the surgical saw blade may have a distal end having at least one pair of teeth configured to be adjacent to each other and each of the pair of teeth is configured as a right triangle each having a hypotenuse which is oriented at least one of towards and away from the centrally positioned long axis.

2. Description of the Prior Art

One of the most vexing problems that surgeons face when using surgical bone saws is the tendency of the saw to "kick" i.e., become caught upon the bone being cut by the point of the saw tooth. Another form of kicking occurs where the kerf has the same contour as the blade which is due to the fact that the cutting surface (i.e., teeth) lies on the same radius as the radius of tool rotation. In this scenario, all teeth grab nearly at the same time. This causes the saw apparatus to rotate about that point, transmitting a rotational force back through the saw and to the surgeon. This kicking or grabbing that occurs causes a loss of accuracy in the cut from the sudden, unpredictable movements of the saw and induces increased fatigue of the surgeon because of the greater tension that the surgeon must maintain in his hands and arms in anticipation of receiving this kicking or grabbing motion.

Another problem noted in existing blades involves the tendency of the saw to initially wander rather than to form a kerf. One reason for this involves the nature of oscillatory cutter blades. The handle portion of the saw remains stable because it is in the surgeon's control and remote from the cutting. However a blade (having a proximal end mounted into the oscillatory power tool) moves at a distal end that scribes an arc of a circle. Most surgical cutting saw blades have teeth on the distal extremity which are also oriented in an arc of constant radius. Especially when that arc has a geometrical center which coincides with the center of oscillatory motion, the bone to be penetrated is normally initially addressed by only one active cutting tooth in the series of teeth that resides on the arc, and as the blade completes its outward motion many teeth come into contact simultaneously. With several teeth contacting the bone, there is a greater tendency of the saw blade to kick and wander. The effect is even more pronounced when the blade teeth's center of arc is between the oscillatory center of the power tool and the blade's distal end.

Another problem involves the non-aggressive nature of prior art blades. Even when more than one tooth contacts the bone, it is primarily due to the manipulation of the blade by the surgeon. The effect is that adjacent teeth do not effect progressive cutting and therefore make binding and kick back more likely.

Moreover, once the kerf has formed, several other problems attend the cutting process. For one thing, substantially all the saw's teeth traverse along the entire extent, of the kerf. This decreases the aggressiveness of the cutting action as the cutting action is an abrading one rather than chipping. The teeth reside within the kerf for a longer period of time and tend to naturally generate more heat than had they been allowed outside the kerf. In addition, not having the teeth exit the working surface periodically tends to leave the chips of bone that have been abraded by the teeth to remain between the teeth. Lack of efficient chip removal is recognized as one cause of excessive heat generation. In surgical situations, such unwanted heat generation is undesirable because of thermal necrosis which damages bone structure adjacent to the cut.

The following documents reflect the state of the art of which applicants are aware and are tendered herewith to discharge the applicants' acknowledged duty to disclose relevant prior art of which they are aware. However, it is respectfully stipulated that none of these prior art teachings anticipate when considered singly or render obvious when considered in any conceivable combination the nexus of the instant invention as particularly detailed hereinafter.

| INVENTOR | U.S. Pat. No. | ISSUE DATE |
| --- | --- | --- |
| Carroll | 2,455,655 | 1948 |
| Tuke | 3,905,105 | 1975 |
| Winter | 3,905,374 | 1975 |
| Bent | 3,943,934 | 1976 |
| Mongeon | 4,386,609 | 1983 |
| Arnegger | 4,513,742 | 1985 |
| Arnegger | 4,584,999 | 1986 |

| CATALOG | TITLE |
| --- | --- |
| Micro-Aire.sup.tmCatalog | "Accessories—Orthopedic Power Instrument System" |
| Stryker* Surgical Catalog | "Cutting Accessories Guide" |
| Hall Surgical Catalog | "Hall Quality Saw Blades for Stryker and 3M" |

None of the prior art explicitly recognizes the value in having the teeth on an oscillatory cutter placed substantially on a tangent which is perpendicular to a radial line extending from the center of the power tools cutting axis that bisects the arc of travel within which the blade travels.

BRIEF SUMMARY OF THE INVENTION

The instant invention is distinguished over the known prior art in a multiplicity of ways.

In its essence, the blade of the instant invention takes into consideration the natural tendencies at play when a surgeon is cutting a bone with an oscillatory saw. In general, the natural tendency is to make a plunge type cut, i.e., move the tool and blade in a single direction, plunging the saw in the bone for cutting. The direction of force imposed by the surgeon is intuitively coaxial with the long axis of the saw and blade. When viewed in this light, it should be clear that prior art cutting blades having curved cutting heads will cause the tip of the tooth to either wander or kick. The instant invention, however, addresses the bone to be cut in a manner which reduces fatigue by the surgeon and vibration or impulses generated during the cutting process.

More specifically, when a tooth profile parallels tangents to the arc of travel of the oscillatory cutter, the bone to be cut sees approximately one tooth at a time when the surgeon is making a plunge into the bone. Actually, the contact starts at the center and moves outwards. In this way, there is less pulsed vibration, there is a lower tendency of the saw to kick by having one tooth engage the bone and rotating thereabout, and there is better bone chip evacuation which reduces the operating temperature of the saw adjacent the cut.

One attribute of the instant invention is that each working tooth progressively cuts more material than the previous working tooth so that collectively, all teeth contacting the bone to be cut make progressive contributions.

Three types of saw blades illustrative of these phenomena are disclosed in the instant application. One blade includes a series of cutting tips all oriented in a linear plane and the teeth which support these tips all have the general configuration of isosceles triangles.

A second form of cutting tool is disclosed in which the tips of all of the teeth are also substantially in a horizontal plane, but the teeth which support these tips have a different contour from the first version. A central-most tooth may be in the form of an isosceles triangle as in the first invention form, but the remaining teeth disposed outboard the central isosceles tooth are all substantially right triangles in which the vertical leg of the right triangle is oriented adjacent the central isosceles tooth and the hypotenuse portion is outboard from the central isosceles tooth. This provides a positive rake, and the most aggressive cut as the blade cuts progressively from the inside out.

A third form of cutting blade is shown in which the right triangles of the second version have been oriented 180° so that the hypotenuse of each cutting tooth faces the center of the cutting blade. In practice, the "right" triangles may be "near" right triangles with the included angle greater than 90° for an aggressive cut. The cutting occurs on the tip of the hypotenuse. Also, there is a central isosceles void provided where there had been the central tooth of the second invention form.

In an alternative, the cutting blade may have a distal end having at least one pair of teeth having tips configured to be adjacent to each other and positioned one on each side of the elongated central axis of the blade. Each of the pair of teeth is configured as a right triangle each having a hypotenuse which is oriented at least one of towards and away from the centrally positioned long axis.

Accordingly, it is the primary object of the present invention to provide a novel and useful cutting saw blade for use in surgery.

A further object of the present invention is to provide a device as characterized above which minimizes the degree of heat buildup associated with the surgical cutting to reduce the thermal necrosis that attends cutting bone.

A further object of the present invention is to provide a device as characterized above which minimizes the backlash and kick that the surgeon experiences when using traditional blades.

A further object of the present invention is to provide a device as characterized above which can be relatively economically manufactured, lends itself to mass production techniques and is extremely durable in construction.

A further object of the present invention is to provide a device as characterized above which cuts aggressively and has a tendency to initially form a kerf, and self centers itself and cuts through the bone quickly within which the blade will reside.

A further object of the present invention is to provide a surgical saw blade having a centrally positioned long axis, a proximal end configured to couple to a surgical bone saw and a distal end having at least one pair of teeth having tips for cutting bone which are configured to be adjacent to each other and wherein one of the pair of teeth is configured as a right triangle with a hypotenuse which is oriented at least one of towards and away from the centrally positioned long axis and the other of the pair of teeth configured as a right triangle with a hypotenuse which is oriented in a direction opposite to the hypotenuse of the one of the pair of teeth.

A further object of the present invention is to provide a surgical saw blade having at least one pair of teeth having tips for cutting bone which are configured to be adjacent to each other and wherein the distal end has extending from each of the pair of teeth at least one additional tooth having a tip for cutting bone which is substantially identically shaped as a right triangle including a hypotenuse and an angle opposite the hypotenuse with a hypotenuse which is oriented in the same direction as the hypotenuse of the adjacent tooth defining the pair of teeth and wherein the tips of all of the teeth are arrayed substantially on a tangent perpendicular to the centrally positioned long axis.

A further object of the present invention is to provide a surgical saw blade having between at least two additional teeth having tips and up to five additional teeth having tips for cutting bone all of which are substantially identically shaped as a right triangle including a hypotenuse and an angle opposite the hypotenuse with a hypotenuse which is oriented in the same direction as the hypotenuse of the adjacent tooth defining the pair of teeth and wherein the tips of all of the teeth are arrayed substantially on a tangent perpendicular to the centrally positioned long axis.

Viewed from one vantage point, it is an object of the present invention to provide a surgical cutting saw blade for penetrating bone when the blade is operatively coupled to an oscillatory power tool. The saw blade has a proximal end and a distal end. The proximal end has means for attachment to the oscillatory power tool for driving engagement thereby. The distal end has a plurality of cutting teeth oriented such that, initially, the outboard teeth contact the bone to be cut to thereby provide better tracking of the saw when forming a kerf in the bone, and the teeth then cut sequentially as the kerf begins to form to provide faster, aggressive cutting and lower temperature cutting through efficient chip removal.

These and other objects will be made manifest when considering the following detailed specification when taken in conjunction with the appended figures.

BRIEF DESCRIPTION OF THE DRAWINGS

FIG. 3 is a detail of the distal end of the embodiment shown in FIG. 2;

FIG. 4 shows the distal end of a third embodiment;

FIGS. 6A and 6B parallel FIGS. 5A and 5B respectively but show prior art;

FIG. 10 is a top plan view of yet still another embodiment of the present invention wherein the distal end of the saw blade has a tooth structure comprising a center tooth defining a "whale shaped" tooth formed of two opposing right triangles having the axially extending centerline of the saw blade passing therethrough followed on each side thereof with two identically shaped teeth formed of a right triangle having the hypotenuse thereof extending at least one of towards and away from the centerline and the proximal end of the saw blade has a hub structure configured for being driven by a driving member having a single driving pin.

DETAILED DESCRIPTION OF THE INVENTION

Figure 1:
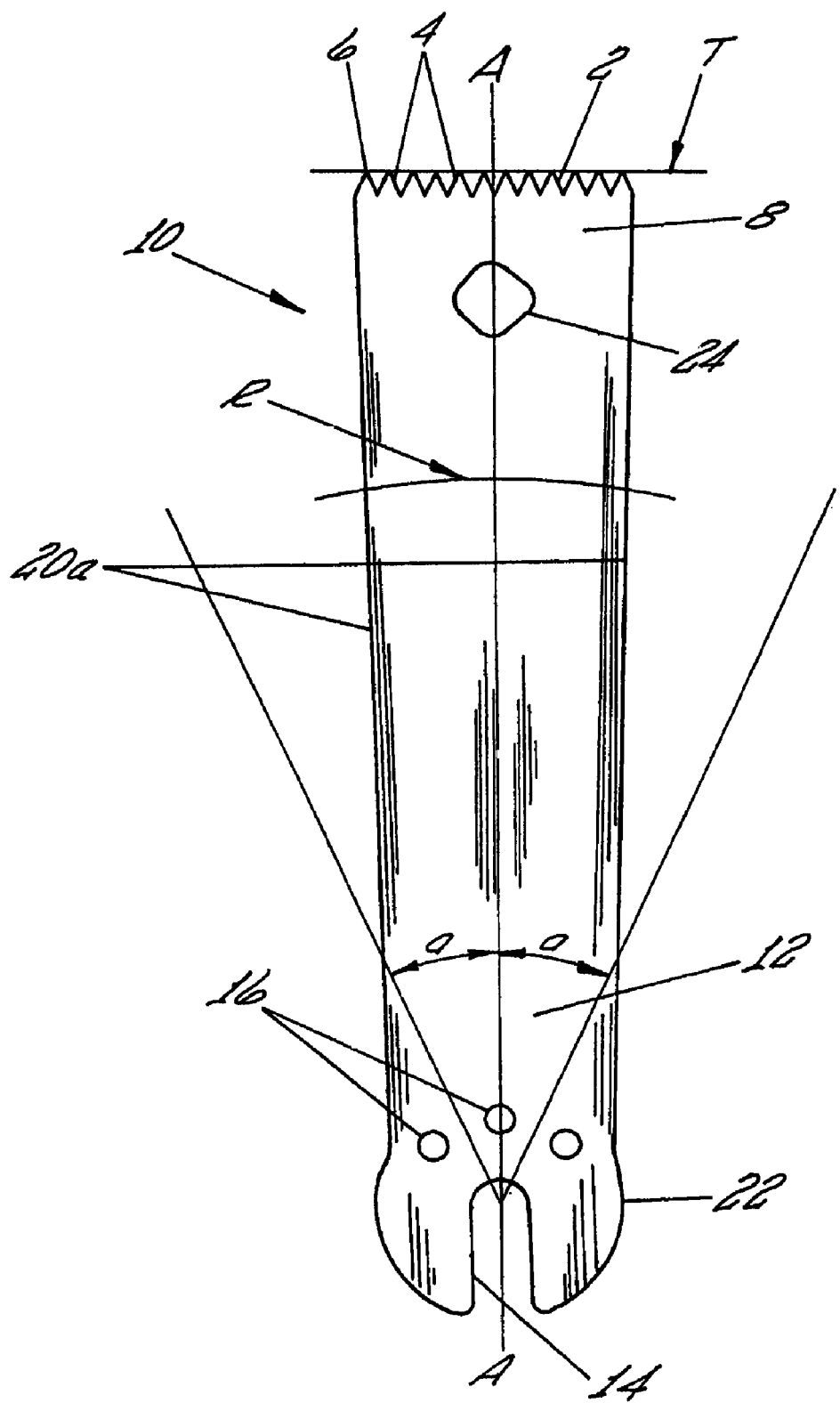
FIG. 1 is a top plan view of the apparatus according to one embodiment of the present invention.

Referring now to the figures, wherein like reference numerals denote to like parts throughout the various figures, reference numeral 10 is directed to the straight saw blade according to one form of the invention, reference numeral 30 is directed to the reverse opposed blade according to the second form of the invention and reference numeral 40 is directed to the outwardly opposed blade according to a third form of the invention.

The straight saw blade 10 of FIG. 1 and according to the present invention includes a distal end 8 upon which a plurality of teeth 2 are positioned and a proximal end 12 which is adapted to coact with and attach to an oscillatory (or sagittal) surgical power tool (not shown).

More specifically, the proximal end 12 has a somewhat bulbous terminus 22 that includes a slot 14 running along the long axis A of the saw blade 10. In addition, a plurality of holes 16 circumscribe portions of the slot adjacent the bulbous terminus 22 to further facilitate interconnection between the saw blade 10 and the oscillatory power tool.

The blade 10 includes a shank 18 interposed between the proximal end 12 and the distal end 8. In general, the shank 18 is formed from substantially flat stock material having side edges 20a which, as shown in FIG. 1, are tapering so that the blade narrows as it goes from the distal end 8 to the proximal end 12.

The distal end 8 of the blade 10 includes, coincident with the long axis A of the blade 10, a diamond shaped cutout 24 having radiused apices at the corners of the diamond. The diamond shaped cutout is oriented such that two of the four radiused apices are coincident with the long axis A of the shank 18. In addition to providing a lighter blade, the diamond shaped orientation tends to assist in tooth profiling during fabrication.

As mentioned, the distal end 8 of the saw blade 10 includes a plurality of teeth 2 disposed on the distal end of the blade 10 remote from the slot 14. Each of the teeth 2 is formed from two sides 4, which coalesce to form the tooth 2. The area of coalescence is defined as tip 6.

As shown in FIG. 1, each of the teeth 2 are formed as isosceles triangles having all tips 6 located on a line T which is tangential to the oscillatory rotation R shown in FIG. 1. Thus, the tips 6 terminate on the tangent line T which is perpendicular to the longitudinal axis A of the cutting blade 10. This is measured when the blade is at an angle which is one-half its maximum arc swing. Typically, an oscillating power tool swings through an arc of 2° to 8° and at speeds ranging from 10,000 cycles per minute to 30,000 cycles per minute.

Figure 2:
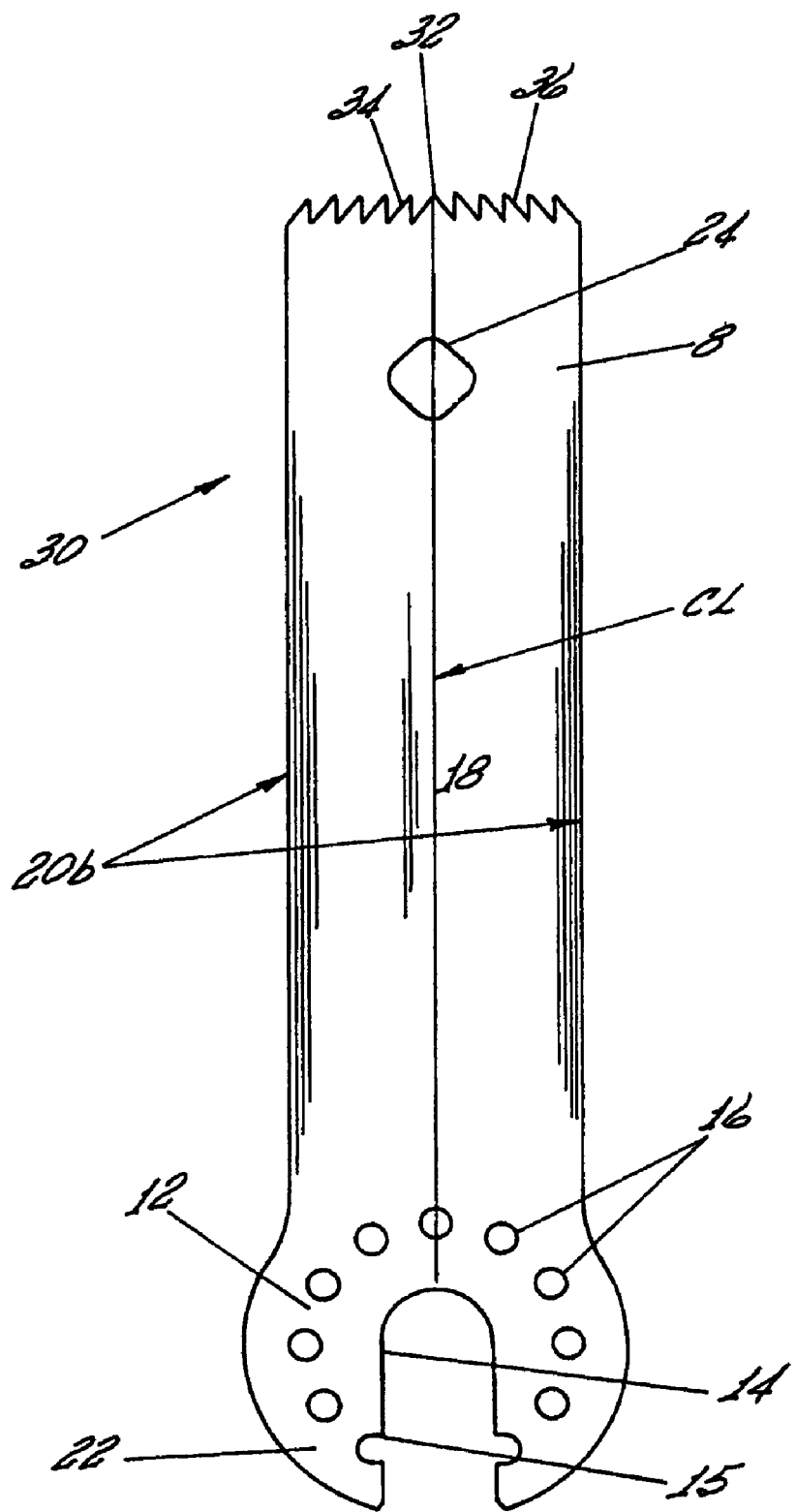
FIG. 2 is a top plan view of a second embodiment similar to FIG. 1.

In a preferred form of the invention, attention is now directed to FIG. 2 which shows a variant of that which is shown in FIG. 1. Tooth details for FIG. 2 are shown in FIG. 3. As shown in FIG. 2, the blade 30 is generally characterized as one which is "reverse opposed" i.e., having a plurality of teeth which are inwardly directed such that when a centerline CL is drawn through the long axis of the blade, two sets of inwardly directed teeth will be evidenced. Those teeth which are to one side of the centerline face those teeth on the other side and are opposed to each other.

The blade 30 also shows that the proximal end 12 includes a bulbous terminus 22 as described with respect to FIG. 1 but in addition to the slot 14 running parallel to the long axis or center line CL, a pair of recesses 15 extend inwardly on linear portions of the U-shaped slot for additional attachment to the oscillatory power tool. Moreover, additional holes 16 circumscribe the U-shaped slot 14 to provide additional retention and drive points when connected to the oscillatory power tool.

The shank 18 is formed from flat stock material whose side edges 20b extend from the distal end 8 to the proximal end 12 but, unlike FIG. 1, these side edges 20b are parallel.

With respect to FIG. 3, certain details of the tooth configuration can also now be best appreciated. As shown, the centerline reflects that one central tooth 32 has an apex or tip coincident with the centerline CL of the long axis of the blade 30. Thus, the central tooth 32 is depicted as forming a substantially isosceles triangle similar to the teeth 2 shown in FIG. 1. However, the centerline CL serves as a line of demarcation between the left lateral side of blade 30 and the right lateral side of blade 30. As shown, the left lateral side includes a plurality of inwardly (i.e. towards central tooth 32) canted teeth 34. Conversely, the right lateral teeth 36 are also inwardly canted toward the central isosceles tooth 32. Both of the left lateral teeth 34 and right lateral teeth 36 are formed substantially as right triangles with the right angle denoted by p. Actually p can be slightly greater than 90° to provide a positive tooth rake when cutting.

Figure 5A:
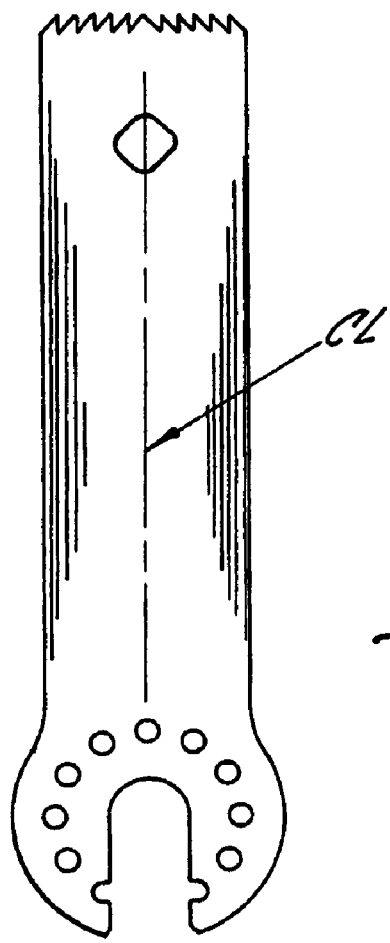
FIG. 5A diagrammatically shows the blade of the present invention posed to begin a cut.
Figure 5B:
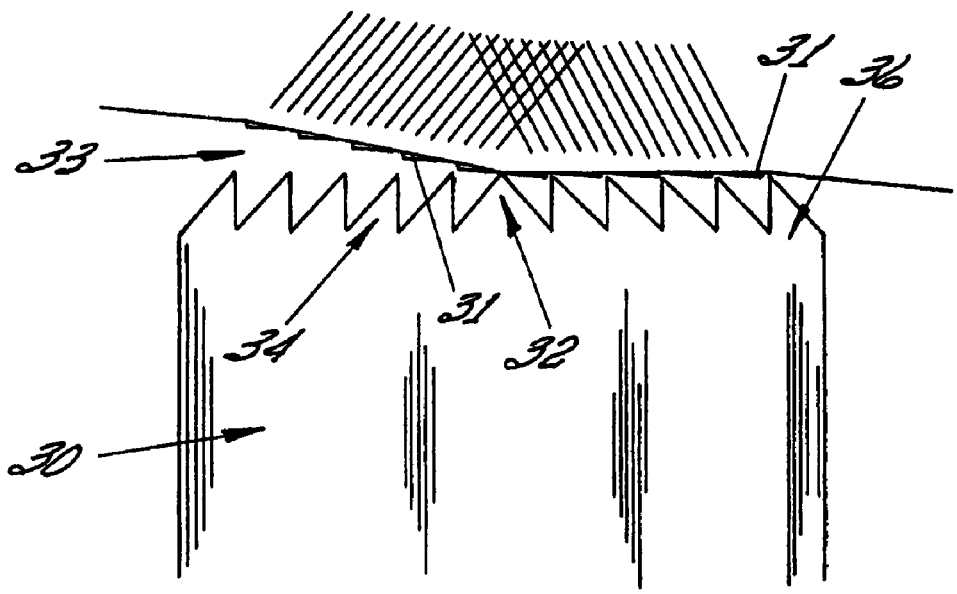
FIG. 5B shows the FIG. 5A blade having progressed partially through a cut.

The hypotenuse leg H of each tooth 34 and 36 is outboard with respect to its vertical leg V. As shown, when p is greater than 90°, leg V slopes towards the centerline CL providing a positive rake. In this manner, teeth 34 and 36 on opposite sides of the central tooth 32 "oppose" each other when cutting. In cutting, FIG. 5A shows the blade poised and oriented tangential to the bone and the teeth perpendicular to the center line CL. FIG. 5B shows the cut after progress has been made in the cut. The cut has been exaggerated to explain the effect.

The kerf 33 is actually V shaped about central tooth 32. As the right side teeth 36 cuts (FIG. 5B), the left side teeth 34 are cooling and cleaning. As shown, the last tooth 36 has just finished cutting and the tooth labeled 34 is about to begin a cut. In effect, each tooth progressively takes a small cut 31 on each oscillatory stroke from the center then laterally outwards. This can be viewed as "progressive staircasing" with the stairs 31 being removed one at a time. Stated alternatively, FIG. 5B shows a blade 30 in an advanced stroke of oscillation where the staircase of material on the left side of the center tooth 32 has already been removed (in an earlier stroke). Then the blade goes into this advanced stroke and has just completely finished this stroke where tooth 36 has stopped its leftward or inward motion and this progressive staircase looking kerf has been formed. As can be envisioned, when the left side teeth 34 are working, the right side teeth 36 are cooling and being cleaned of chips. A very slight V shaped kerf is formed in practice.

The active cutting tip 6 is the end of the vertical leg V where it contacts leg H. The central tooth 32 is optional. Note the teeth in the FIG. 3 embodiment also terminate along a tangent line T which is at right angles to the centerline CL.

With respect to FIG. 4, it is to be observed that the proximal end of the FIG. 4 version has not been shown. This is due to the fact that it could be accommodated by many commercially available or by either the FIG. 1 or the FIG. 2 variants and will not be belabored here. However, the distal end 8 of the FIG. 4 version bears some differences which need to be addressed. This version 40 is distinguished from the first version 10 and second version 30 by including a plurality of outwardly opposed teeth.

More specifically, the centerline CL of the FIG. 4 version 40 serves as a line of demarcation between the left side teeth 44 and the right side teeth 46. The centerline CL, when bisecting between the left side teeth 44 and the right side teeth 46, passes through a central isosceles void 42 (i.e. the absence of a central tooth). The tooth structure 44 and 46 is similar to the FIGS. 2 and 3 structure. However, the hypotenuse leg H of these triangles has been transposed 180 so that this leg now faces the central isosceles void 42 and the vertical leg V is canted slightly to the "outside", i.e. away from the center line CL and center isosceles void 42, providing a negative rake. Using this structure, it is possible to appreciate that the teeth 44 and 46 according to this version work opposite from the teeth 44 and 46 shown in FIGS. 2 and 3. However, all teeth in all versions are substantially "flat-top" configured, i.e., the tips stop at the tangent T perpendicular to the center line CL. Note the tip 48 of the outermost teeth 44 and 46 extend beyond the side edges 20c. The aggressive cutting pattern of the blade 40 shown in FIG. 4 has excellent chip clearing properties analogous to FIG. 5B, but opposite therefrom.

Prior art FIGS. 6A and 6B show the effect of cutting teeth on a curve such that the radius r falls between the oscillatory axis 0 and the distal end 8. In use, only very few teeth actually do the cutting work and the cutting is not progressively advanced. As "r" gets larger—approaching the "flat-top" structure preferred in the instant invention, more teeth get progressively involved in the cutting. As show in FIG. 6B, tooth contact is not progressive as in FIG. 5B.

Moreover, having thus described the invention, it should be apparent that numerous structural modifications and adaptations may be resorted to without departing from the scope and fair meaning of the instant invention as set forth hereinabove and as claimed hereinbelow.

Alternative Embodiments of Surgical Saw Blades

Figure 7:
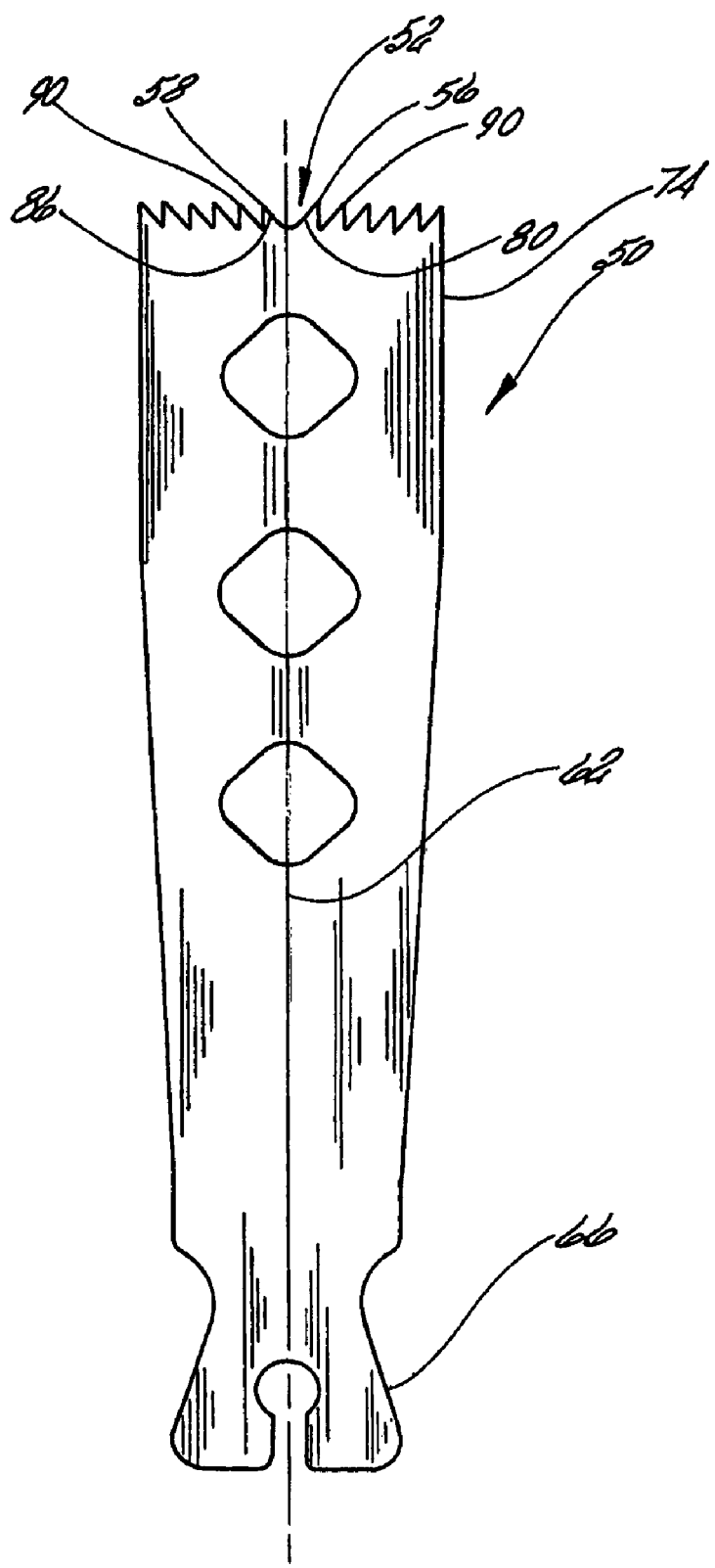
FIG. 7 is a top plan view of another embodiment of the present invention wherein the saw blade has a tooth structure comprising a center tooth defining a "whale shaped" tooth formed of two opposing right triangles having tips and located to have the axially extending centerline of the saw blade passing therethrough followed on each side thereof with five identically shaped teeth having tips formed of a right triangle having tips and located to have the hypotenuse thereof extending at least one of towards and away from the center line.

The top plan view of FIG. 7 illustrates another embodiment or species of the present invention wherein the surgical saw blade 50 has a tooth structure comprising a center tooth 52 defining a "whale shaped" tooth formed of two opposing right triangles 56 and 58 having an axially extending centerline or a centrally positioned long axis 62 of the surgical saw blade passing there through.

The surgical saw blade 50 includes a proximal end 66 configured to couple to a surgical bone saw. The surgical saw blade 50 includes a distal end 74 having at least one pair of teeth 56 and 58 for cutting bone. The at least one pair of teeth 56 and 58 having tips are configured to be adjacent to each other and each tooth is configured as a right triangle with a hypotenuse which is oriented at least one of towards and away from the centrally positioned long axis. The one tooth 56 has a hypotenuse 80 which is oriented at least one of towards and away from the centrally positioned long axis. The other of the pair of teeth 58 is configured as a right triangle with a hypotenuse 86 which is oriented in a direction opposite to the hypotenuse of the one tooth 56 of the pair of teeth. The tips of the teeth 56 and 58 are arrayed substantially on a tangent perpendicular to the centrally positioned long axis 62. The distal end 74 has extending from each of the pair of teeth 56 and 58 at least one additional tooth 90 having a tip for cutting bone which is substantially identically shaped as a right triangle including a hypotenuse and an angle opposite the hypotenuse with a hypotenuse which is oriented in the same direction as the hypotenuse of the adjacent tooth defining the pair of teeth. The tips of all of the teeth 56, 58 and 90 are arrayed substantially on a tangent perpendicular to the centrally positioned long axis.

In FIG. 7, this species of the surgical saw blade has a pair of opposed teeth 56 and 58 and five additional teeth 90 having tips extending from each of the pair of teeth 56 and 58. The proximal end 66 has a hub that is configured to be driven by a saw having a single driving pin.

Figure 8:
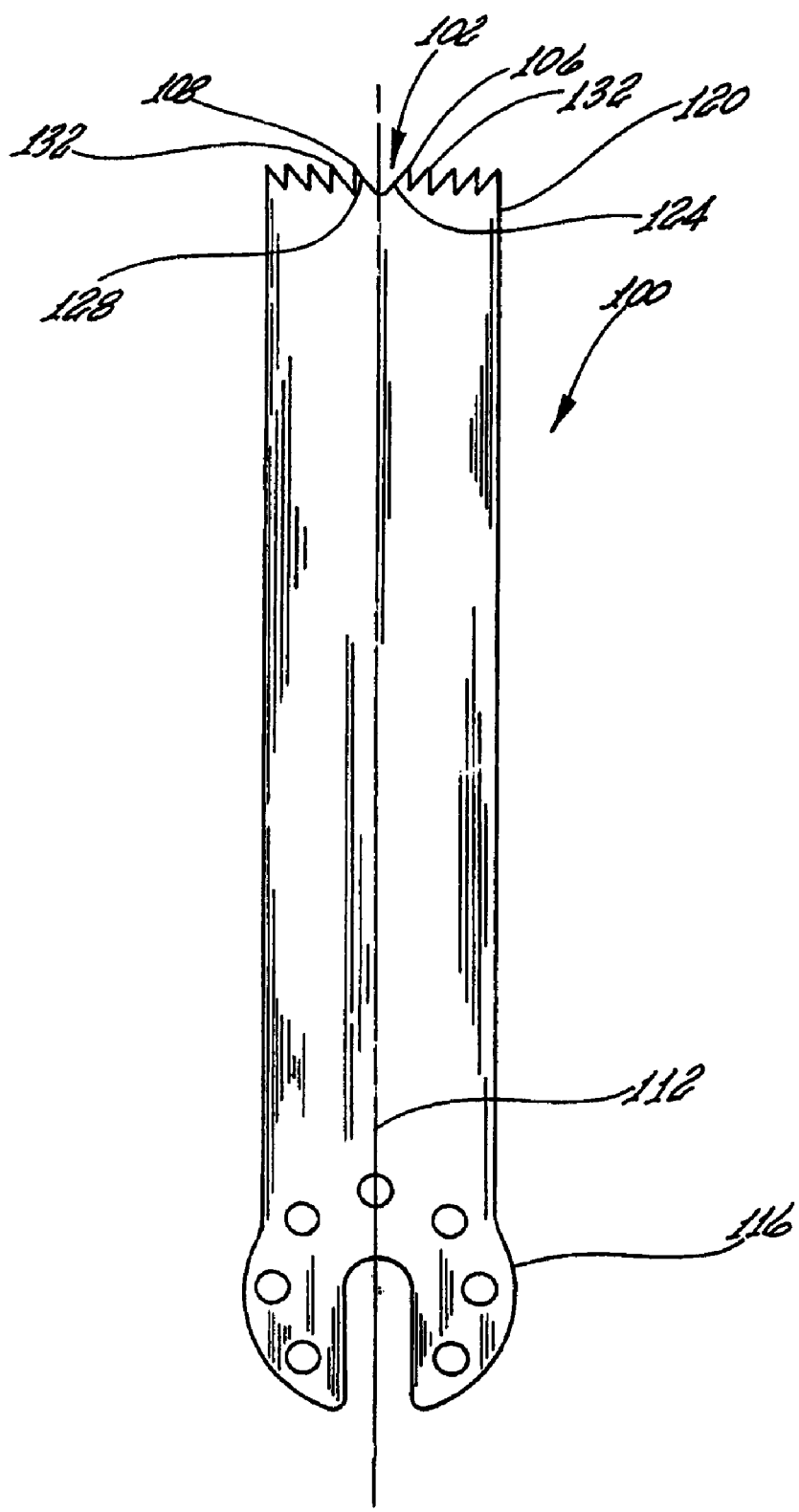
FIG. 8 is a top plan view of yet another embodiment of the present invention wherein the saw blade has a tooth structure comprising a center tooth defining a "whale shaped" tooth formed of two opposing right triangles having tips and located to have the axially extending centerline of the saw blade passing therethrough followed on each side thereof with four identically shaped teeth having tips formed of a right triangle having the hypotenuse thereof extending at least one of towards and away from the centerline.

The top plan view of FIG. 8 illustrates yet another embodiment or species of the present invention wherein the surgical saw blade 100 has a tooth structure comprising a center tooth 102 defining a "whale shaped" tooth formed of two opposing right triangles 106 and 108 having an axially extending centerline or a centrally positioned long axis 112 of the surgical saw blade passing there through.

The surgical saw blade 100 includes a proximal end 116 configured to couple to a surgical bone saw. The surgical saw blade 100 includes a distal end 120 having at least one pair of teeth 106 and 108 having tips for cutting bone. The at least one pair of teeth 106 and 108 are configured to be adjacent to each other and each tooth is configured as a right triangle with a hypotenuse which is oriented at least one of towards and away from the centrally positioned long axis. The one tooth 106 has a hypotenuse 124 which is oriented at least one of towards and away from the centrally positioned long axis. The other of the pair of teeth 108 is configured as a right triangle with a hypotenuse 128 which is oriented in a direction opposite to the hypotenuse of the one tooth 106 of the pair of teeth. The tips of the teeth 106 and 108 are arrayed substantially on a tangent perpendicular to the centrally positioned long axis 112. The distal end 116 has extending from each of the pair of teeth 106 and 108 at least one additional tooth 132 having a tip for cutting bone which is substantially identically shaped as a right triangle including a hypotenuse and an angle opposite the hypotenuse with a hypotenuse which is oriented in the same direction as the hypotenuse of the adjacent tooth defining the pair of teeth. The tips of all of the teeth 106, 108 and 132 are arrayed substantially on a tangent perpendicular to the centrally positioned long axis.

In FIG. 8, this species of the surgical saw blade has a pair of opposed teeth 106 and 108 and four additional teeth 132 having tips extending from each of the pair of teeth 106 and 108. The proximal end 116 has a hub that is configured to be driven by a saw having a multiple pin driver.

Figure 9:
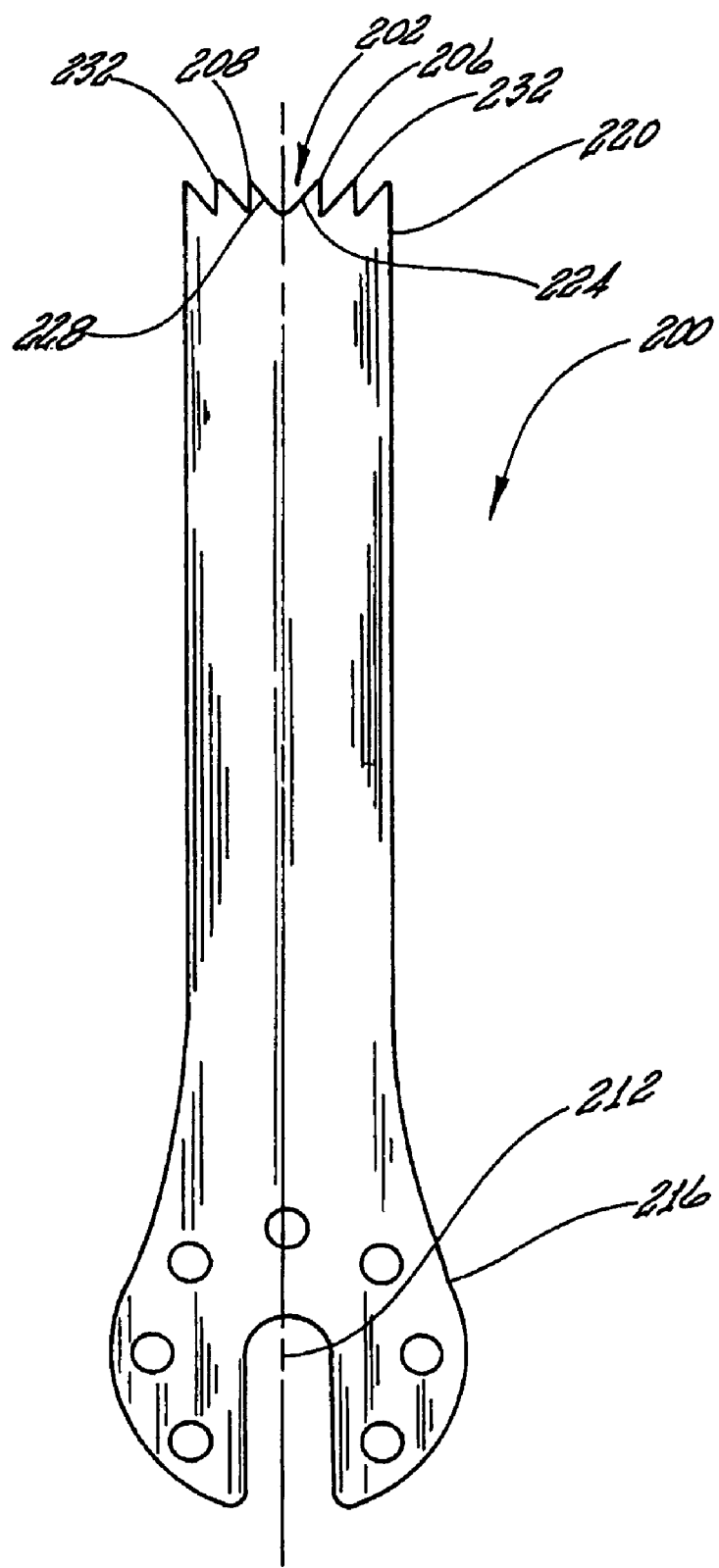
FIG. 9 is a top plan view of still yet another embodiment of the present invention wherein the distal end of the saw blade has a tooth structure comprising a center tooth defining a "whale shaped" tooth formed of two opposing right triangles having tips and located to have the axially extending centerline of the saw blade passing therethrough followed on each side thereof with two identically shaped teeth formed of a right triangle having the hypotenuse thereof extending at least one of towards and away from the centerline and the proximal end of the saw blade has a hub structure configured for being driven by a driving member having driving pins.

The top plan view of FIG. 9 illustrates still yet another embodiment or species of the present invention wherein the surgical saw blade 200 has a tooth structure comprising a center tooth 202 defining a "whale shaped" tooth formed of two opposing right triangles 206 and 208 having an axially extending centerline or a centrally positioned long axis 212 of the surgical saw blade passing there through.

The surgical saw blade 200 includes a proximal end 216 configured to couple to a surgical bone saw. The surgical saw blade 200 includes a distal end 220 having at least one pair of teeth 206 and 208 having tips for cutting bone. The at least one pair of teeth 206 and 208 are configured to be adjacent to each other and each tooth is configured as a right triangle with a hypotenuse which is oriented at least one of towards and away from the centrally positioned long axis. The one tooth 206 has a hypotenuse 224 which is oriented at least one of towards and away from the centrally positioned long axis. The other of the pair of teeth 208 is configured as a right triangle with a hypotenuse 228 which is oriented in a direction opposite to the hypotenuse of the one tooth 206 of the pair of teeth. The tips of the teeth 206 and 208 are arrayed substantially on a tangent perpendicular to the centrally positioned long axis 212. The distal end 216 has extending from each of the pair of teeth 206 and 208 at least one additional tooth 232 having a tip for cutting bone which is substantially identically shaped as a right triangle including a hypotenuse and an angle opposite the hypotenuse with a hypotenuse which is oriented in the same direction as the hypotenuse of the adjacent tooth defining the pair of teeth. The tips of all of the teeth 206, 208 and 232 are arrayed substantially on a tangent perpendicular to the centrally positioned long axis.

In FIG. 9, this species of the surgical saw blade has a pair of opposed teeth 206 and 208 and two additional teeth 232 extending from each of the pair of teeth 206 and 208. The proximal end 216 has a hub that is configured to be driven by a saw having a multiple pin driver.

The top plan view of FIG. 10 illustrates yet still another embodiment or species of the present invention wherein the surgical saw blade 300 has a tooth structure comprising a center tooth 302 defining a "whale shaped" tooth formed of two opposing right triangles 306 and 308 having an axially extending centerline or a centrally positioned long axis 312 of the surgical saw blade passing there through.

The surgical saw blade 300 includes a proximal end 316 configured to couple to a surgical bone saw. The surgical saw blade 300 includes a distal end 320 having at least one pair of teeth 306 and 308 having tips, for cutting bone. The at least one pair of teeth 306 and 308 are configured to be adjacent to each other and each tooth is configured as a right triangle with a hypotenuse which is oriented at least one of towards and away from the centrally positioned long axis. The one tooth 306 has a hypotenuse 324 which is oriented at least one of towards and away from the centrally positioned long axis. The other of the pair of teeth 308 is configured as a right triangle with a hypotenuse 328 which is oriented in a direction opposite to the hypotenuse of the one tooth 306 of the pair of teeth. The tips of the teeth 306 and 308 are arrayed substantially on a tangent perpendicular to the centrally positioned long axis 212. The distal end 216 has extending from each of the pair of teeth 306 and 308 at least one additional tooth 332 having a tip for cutting bone which is substantially identically shaped as a right triangle including a hypotenuse and an angle opposite the hypotenuse with a hypotenuse which is oriented in the same direction as the hypotenuse of the adjacent tooth defining the pair of teeth. The tips of all of the teeth 306, 308 and 332 are arrayed substantially on a tangent perpendicular to the centrally positioned long axis.

In FIG. 10, this species of the surgical saw blade has a pair of opposed teeth 306 and 308 and two additional teeth 332 having tips extending from each of the pair of teeth 306 and 308. The proximal end 316 has a hub that is configured to be driven by a saw having a single pin driver.

As discussed above in connection with FIG. 7, the distal end 74 of surgical saw blade 50 has extending from each of the pair of teeth 56 and 58 has at least one additional tooth 90 for cutting bone which is substantially identically shaped as a right triangle as the teeth 56 and 58 including a hypotenuse and an angle opposite the hypotenuse with the hypotenuse oriented in the same direction as the hypotenuse of the adjacent tooth 56 or 58 defining the pair of teeth. All of the tips of all of the teeth 56, 58 and 90 are arrayed substantially on a tangent perpendicular to the centrally positioned long axis.

As illustrated in FIG. 7, the number of additional teeth can be a number for at least two additional teeth having tips to five additional teeth having tips.

In the species of FIGS. 7 through 10, the surgical saw blade illustrated therein are for use in combination with a surgical bone saw. In FIG. 8, for example, the surgical saw blade 100 comprises a proximal end 116 which is configured to couple to a surgical bone saw. The surgical saw blade 100 includes a distal end 120 having a plurality of substantially identical teeth having tips for cutting bone. Each of the plurality of teeth end in a tip distally.

The surgical saw blade includes a centrally positioned long axis 112 extending between the proximal end 116 and the distal end 120. At the distal end 120, the a plurality of substantially identical teeth for cutting bone include at least one pair of teeth 106 and 108 for cutting bone which are configured to be adjacent to each other and wherein one of the pair of teeth, tooth 106, has a hypotenuse 124 which is oriented at least one of towards and away from the centrally positioned long axis 112. The other of the pair of teeth, tooth 108, has a hypotenuse 128 which is oriented in a direction opposite to the hypotenuse 128 of the one of the pair of teeth 106 and the tips thereof are arrayed substantially on a tangent perpendicular to the centrally positioned long axis.

The distal end 120 has extending from each of the pair of teeth 106 and 108 at least one additional tooth 132 for cutting bone which is substantially identically shaped as a right triangle including a hypotenuse and an angle opposite the hypotenuse with a hypotenuse which is oriented in the same direction as the hypotenuse of its adjacent tooth defining the pair of teeth 106 and 108. The tips of all of the teeth 106, 108 and 132 are arrayed substantially on a tangent perpendicular to the centrally positioned long axis.

As illustrated in FIGS. 7 through 10, the at least one additional tooth may be a single tooth having a tip or a number of teeth having tips which is at least two additional teeth to five additional teeth. Each of the additional teeth, teeth 132 in FIG. 8 being exemplary, are substantially identically shaped as a right triangle including a hypotenuse and an angle opposite the hypotenuse and the hypotenuse thereof is oriented in the same direction as the hypotenuse of the adjacent tooth of the pair of teeth 106 and 108, respectively. The tips of all of the teeth are arrayed substantially on a tangent perpendicular to the centrally positioned long axis. By having all of the tips of the teeth configured to be placed substantially on a tangent which is perpendicular to a radial line extending from the center line of the power tool cutting axis that bisects the arc of travel within which the blade travels represented by the centrally extending long axis illustrated in FIGS. 7 through 10, the teeth are enabled to contact the bone to be cut and thereby and provide better tracking of the surgical saw blade when forming a kerf in the bone, as such, the teeth cut both progressively and sequentially as the kerf begins to form to provide faster aggressive cutting and efficient chip removal.

In FIGS. 7 through 10, the angle opposite each hypotenuse is greater than 90°.

Each of the species of the surgical saw blade illustrated in FIGS. 7 through 10 can be used in a method of cutting bone. The method comprises the steps of: a) providing a surgical saw blade having a proximal end configured to couple to a surgical bone saw, a distal end having a plurality of substantially identical teeth having tips for cutting bone, each of the plurality of teeth ending in a tip distally and a centrally positioned long axis between the proximal end and the distal end and wherein said distal end has a plurality of substantially identical teeth having tips for cutting bone including at least one pair of teeth for cutting bone which are configured to be adjacent to each other and wherein one of the pair of teeth has a hypotenuse which is oriented at least one of towards and away from the centrally positioned long axis and the other of said pair of teeth has a hypotenuse which is oriented in a direction opposite to the hypotenuse of the one of the pair of teeth and wherein the tips are arrayed substantially on a tangent perpendicular to the centrally positioned long axis, and wherein said distal end has extending from each of said pair of teeth at least one additional tooth having a tip for cutting bone which is substantially identically shaped as a right triangle including a hypotenuse and an angle opposite the hypotenuse with a hypotenuse which is oriented in the as the hypotenuse of the adjacent tooth defining the pair of teeth and wherein the tips of the additional teeth are arrayed substantially on a tangent perpendicular to the centrally positioned long axis; b) coupling the surgical saw blade to a surgical saw; c) actuating the surgical saw with the coupled saw blade; and d) cutting the bone.

The method may include using a surgical saw blade wherein the additional number of teeth of the saw blade provided in step a) are at least two additional teeth having tips.

The method may include using a surgical saw blade wherein the additional number of teeth of the saw blade provided in step a) are between at least two additional teeth having tips and five additional teeth having tips.

The method may include using a surgical saw blade wherein the angle opposite each hypotenuse of the teeth provided in step a) is greater than 90°.

The structures of the surgical saw blades illustrated in FIGS. 7 through 10 provide a surgeon with several variations of surgical saw blades for use in cutting bone as part of a surgical procedure or surgical operation. Specifically, the structure of each of the distal ends of the surgical saw blades of FIGS. 7 through 10 enable the tips of the teeth thereof to contact the bone to be cut thereby and to provide better tracking of the surgical saw blade when forming a kerf in the bone. As such, the teeth cut both progressively and sequentially as the kerf begins to form to provide faster aggressive cutting and efficient chip removal.

If a faster or more rapid cutting of the bone is desired during a surgical procedure, the surgeon may elect to use the surgical saw blade of FIGS. 7 and 8 which have more teeth available to provide faster aggressive cutting and efficient chip removal.

If a more controlled or slower cutting of the bone is desired during a surgical procedure, the surgeon may elect to use the surgical saw blades of FIGS. 9 and 10 which have a lower number of teeth to provide a more controlled aggressive cutting and efficient chip removal.

Lubricious Surface Treatments for Surgical Saw Blades

The coefficient of friction between a surgical saw blade, the bone to be cut and a surgical saw cutting guide, if a cutting guide is used during a surgical procedure, may affect the quality of the final bone cut due to possible sticking or lack of smooth movement of the surgical saw blade during a surgical procedure. It is envisioned that a lubricious surface treatment, such as a coating could be applied to the surgical saw blades, described herein, to reduce the coefficient of friction between a surgical saw blade, the bone to be cut and a surgical accessory, such as for example a surgical saw blade cutting guide.

In order to increase the performance of a surgical saw blade during a surgical procedure, a lubricious surface treatment and or coating material having a composition capable of decreasing the coefficient of friction between a surgical saw blade, the bone to be cut and a surgical accessory is applied to the distal end of the surgical saw blade including the teeth that would be in contact with bone or bone fragments during cutting. This results in a reduction of the coefficient of friction on the outer surface of the saw blade.

In the preferred embodiment, the lubricious surface treatment and or coating material has a Vickers hardness number (HV) of about 820 or above. The coefficient of friction of a surgical saw blade that is untreated or uncoated with a lubricious surface treatment and or coating material is in the range of about 0.25 or more on/against steel. When a lubricious surface treatment and or coating material is applied to the surgical saw blade, using coating techniques the coefficient of friction is lowered to about 0.8 to about 0.20 on/against steel, depending on the composition and physical characteristics of the lubricious surface treatment and or coating material.

The lower coefficient of friction of the lubricious surface treatment and or coating of this invention gives the surgical saw blades a significantly enhanced ability to glide easily between the bone being cut, tissue that comes in contact with the surgical saw blade and interproximal contact between the surgical saw blade and surgical accessory contacted by the surgical saw blade during a procedure such as, for example, a cutting guide.

The following are examples of lubricious surface treatment and or coating materials that can be used to practice this invention.

2EXAMPLES Surface Treatment/Physical Coating Material Composition Description Characteristics Composite Diamond Diamond particles Hardness, corrosion resistance, abrasion resistance Thermal/Plasma Molten Ceramic Permanent non-Spray Ceramic stick, chemical resistant, non-wetting; FDA approved Low-Temp/PVD/CVD Zirconia Nitride, Titanium-Hardness, self-Matrix Carbo Nitride, Titanium lubricating, low Oxide, Titanium Nitride or friction; Chromium Oxide Low-temperature Physical Vapor Deposition or Chemical Vapor Deposition Plasma/Ion Low-temperature surface Hardness, self-Nitriding modification of base lubricating, low Stainless Steel friction The lubricious surface treatment and or coating material may have a selected thickness. If the lubricious surface treatment and or coating material is applied by vacuum deposition or vapor deposition, e.g. PVD, the thickness may be in the order of a few microns (1 .mu.m to 10 .mu.m). On the other hand, if the lubricious surface treatment and or coating material is applied by dipping, spraying, a laminated coating procedures or is applied using other coating procedures known to those skilled in the art, the thickness may be in a range of the order of about 1 mil to about 15 mils.

The examples disclosed herein are intended to cover such applications discussed herein, and it is envisioned that other uses of a surgical saw blade having the structure disclosed and taught herein, including the use of a lubricious surface treatment and or coating material coated thereon, will become apparent to those skilled in the art and all such uses are envisioned to be within the teachings and scope of the present invention.

All such uses, variations, modifications and the like are also anticipated to be within the scope of this invention.

What is claimed is:

1. A surgical saw blade for penetrating bone when said surgical saw blade is operatively coupled to an oscillatory power tool, comprising:
    a surgical saw blade having a proximal end and a distal end;
    said proximal end having a hub for attachment to an oscillatory power tool for driving engagement thereby;
    said distal end having a plurality substantially identically shaped cutting teeth each tooth having a tip configured as a right triangle ending in a distal tip configured to be placed substantially on a tangent which is perpendicular to a radial line extending from the center line of the power tool cutting axis that bisects the arc of travel within which the blade travels such that said teeth contact the bone to be cut thereby to provide better tracking of said surgical saw blade when forming a kerf in the bone, whereupon said teeth cut both progressively and sequentially as the kerf begins to form to provide faster aggressive cutting and efficient chip removal; and
    a lubricious coating material having a Rockwell hardness of about 65 to about 90 being applied to the outer surface of the surgical saw blade.

2. The surgical saw blade of claim 1 wherein said distal end has at least two additional teeth for cutting bone each of which are substantially identically shaped as a right triangle including a hypotenuse and an angle opposite the hypotenuse with the hypotenuse is oriented in the same direction as the hypotenuse of the adjacent tooth defining said pair of teeth and wherein the tips of all of the teeth are arrayed substantially on a tangent perpendicular to the centrally positioned long axis.

3. The surgical saw blade of claim 1 wherein said distal end has at least three additional teeth for cutting bone each of which are substantially identically shaped as a right triangle including a hypotenuse and an angle opposite the hypotenuse wherein each hypotenuse is oriented in the same direction and wherein the tips of all of the teeth are arrayed substantially on a tangent perpendicular to the centrally positioned long axis.

4. The surgical saw blade of claim 1 wherein said distal end has at least four additional teeth for cutting bone each of which are substantially identically shaped as a right triangle including a hypotenuse and an angle opposite the hypotenuse wherein each hypotenuse is oriented in the same direction and wherein the tips of all of the teeth are arrayed substantially on a tangent perpendicular to the centrally positioned long axis.

5. The surgical saw blade of claim 1 wherein said distal end has at least five additional teeth for cutting bone each of which are substantially identically shaped as a right triangle including a hypotenuse and an angle opposite the hypotenuse wherein each hypotenuse is oriented in the same direction and wherein the tips of all of the teeth are arrayed substantially on a tangent perpendicular to the centrally positioned long axis.

6. The surgical saw blade of claim 1 wherein the coefficient of friction of the lubricious coating material is in the range of about 0.08 to about 0.25.

7. The surgical saw blade of claim 1 wherein the lubricious coating material is selected from a group consisting of Composite Diamond, a Teflon/Nickel Composite, an Inorganic Powder/Nickel, a Fluoropolymer, a Fusion bonded fluoropoly, a Thermal Spray Polymer, a PVD Matrix, polytetrafluoroethylene, Fluorinated Ethylene Propylene, Perfluoroalkoxy, Ethylene/Tetrafluoroethylene Copolymer and Antimicrobial Material.

8. A surgical saw blade for penetrating bone when said surgical saw blade is operatively coupled to an oscillatory power tool, comprising:
    a surgical saw blade having a proximal end and a distal end;
    said proximal end having a hub for attachment to an oscillatory power tool for driving engagement thereby;
    said distal end has a first plurality of teeth and a second plurality of teeth ending in a distal tip configured to be placed substantially on a tangent which is perpendicular to a radial line extending from the center line of the power tool cutting axis that bisects the arc of travel within which the blade travels such that said teeth contact the bone to be cut thereby to provide better tracking of said surgical saw blade when forming a kerf in the bone, whereupon said teeth cut both progressively and sequentially as the kerf begins to form to provide faster aggressive cutting and efficient chip removal;
    the first plurality of teeth on one side of the center line and comprising teeth each substantially identically shaped as a right triangle including a hypotenuse and an angle opposite the hypotenuse wherein the hypotenuse is oriented in the same direction as the hypotenuse of each adjacent tooth in the first plurality of teeth and wherein the tips of all of the teeth are arrayed substantially on a tangent perpendicular to the centrally positioned long axis; and
    the second plurality of teeth on an opposite side of the center line and comprising teeth each substantially identically shaped as a right triangle including a hypotenuse and an angle opposite the hypotenuse wherein the hypotenuse is oriented in the same direction as the hypotenuse of each adjacent tooth in the second plurality of teeth and wherein the tips of all of the teeth are arrayed substantially on a tangent perpendicular to the centrally positioned long axis;
    wherein the first plurality of teeth are reverse opposed to the second plurality of teeth so that the hypotenuses of the first plurality of teeth are oriented in a first direction and wherein the hypotenuses of the second plurality of teeth are oriented in a direction opposite the first direction.

9. The surgical saw blade of claim 8 further comprising:
a lubricious coating material having a Rockwell hardness of about 65 to about 90 applied to the outer surface of the surgical saw blade.

10. The surgical saw blade of claim 9 wherein the coefficient of friction of the lubricious coating material is in the range of about 0.08 to about 0.25.

11. The surgical saw blade of claim 9 wherein the lubricious coating material is selected from a group consisting of Composite Diamond, a Teflon/Nickel Composite, an Inorganic Powder/Nickel, a Fluoropolymer, a Fusion bonded fluoropoly, a Thermal Spray Polymer, a PVD Matrix, polytetrafluoroethylene, Fluorinated Ethylene Propylene, Perfluoroalkoxy, Ethylene/Tetrafluoroethylene Copolymer and Anti-microbial Material.

12. The surgical saw blade of claim 8 wherein the hypotenuses of the first plurality of teeth and the second plurality of teeth are each oriented towards the center line.

13. The surgical saw blade of claim 8 wherein the hypotenuses of the first plurality of teeth and the second plurality of teeth are each oriented away from the center line.

* * * * *